United States Patent
Grollier et al.

[11] Patent Number: 5,958,392
[45] Date of Patent: Sep. 28, 1999

[54] COMPOSITION FOR THE TREATMENT OF KERATIN FIBERS, BASED ON AMPHOTERIC POLYMERS AND CATIONIC POLYMERS

[75] Inventors: Jean Francois Grollier; Claire Fiquet; Chantal Fourcadier, all of Paris; Claude Dubief, Versailles; Daniele Cauwet, Crosne, all of France

[73] Assignee: L'Oreal, Paris, France

[21] Appl. No.: 08/487,479

[22] Filed: Jun. 7, 1995

Related U.S. Application Data

[63] Continuation of application No. 07/877,371, Apr. 29, 1992, which is a continuation of application No. 07/623,084, Dec. 6, 1990, abandoned, which is a continuation of application No. 07/498,490, Mar. 26, 1990, Pat. No. 4,996,059, which is a continuation of application No. 06/517,565, Jul. 28, 1983, abandoned, which is a continuation of application No. 06/210,620, Nov. 26, 1980, abandoned.

[30] Foreign Application Priority Data

Nov. 28, 1979 [FR] France ................................. 79 29318

[51] Int. Cl.$^6$ ............................ A61K 7/075; A61K 7/08; A61K 7/09; C11D 3/37
[52] U.S. Cl. ......................... 424/70.17; 424/70.13; 424/70.19; 424/70.27; 424/70.28; 424/486; 424/488; 424/499; 424/501; 424/DIG. 1; 424/DIG. 2; 252/DIG. 13; 510/119; 510/121
[58] Field of Search ..................... 424/400, 70.13, 424/70.19, 70.27, 70.28, 486, 488, 499, 501, DIG. 1, DIG. 2; 252/DIG. 13; 510/119, 121, 123, 124

[56] References Cited

U.S. PATENT DOCUMENTS

| | | | |
|---|---|---|---|
| 3,836,537 | 9/1974 | Boerwinkle | 424/71 X |
| 3,980,769 | 9/1976 | Ghilardi | 424/71 |
| 4,013,787 | 3/1977 | Vanlerberghe | 424/70 |
| 4,031,025 | 6/1977 | Vanlerberghe | 424/47 X |
| 4,075,131 | 2/1978 | Sterling | 424/70 X |
| 4,120,815 | 10/1978 | Raman | 252/341 |
| 4,128,631 | 12/1978 | Lundmark | 424/70 |
| 4,172,887 | 10/1979 | Vanlerberghe | 424/70 |
| 4,189,468 | 2/1980 | Vanlerberghe | 424/70 |
| 4,197,865 | 4/1980 | Jacquet | 132/7 |
| 4,213,960 | 7/1980 | Grollier | 424/47 |
| 4,217,914 | 8/1980 | Jacquet | 132/7 |
| 4,220,548 | 9/1980 | Hashimoto | 252/106 |
| 4,223,009 | 9/1980 | Chakrabarti | 424/47 |
| 4,237,253 | 12/1980 | Jacquet et al. | 526/75 |
| 4,240,450 | 12/1980 | Grollier | 424/70 X |
| 4,243,659 | 1/1981 | Balingit et al. | 424/70 |
| 4,277,581 | 7/1981 | Vanlerberghe | 525/420 |
| 4,324,780 | 4/1982 | Jacquet et al. | 424/47 |
| 4,402,977 | 9/1983 | Grollier et al. | 424/70 |

FOREIGN PATENT DOCUMENTS

| | | | |
|---|---|---|---|
| 2383660 | 12/1978 | France | 424/70 |
| 2817369 | 10/1978 | Germany . | |
| 1021400 | 3/1966 | United Kingdom | 424/70 |
| 1407659 | 9/1975 | United Kingdom | 424/71 |

*Primary Examiner*—Edward J. Webman
*Attorney, Agent, or Firm*—Jacobson, Price, Holman & Stern, PLLC

[57] ABSTRACT

The invention relates to a composition used for the treatment of keratin substances which contains at least one amphoteric polymer containing units A and B randomly distributed in the polymer chain, where A denotes a unit derived from a monomer containing at least one basic nitrogen atom and B denotes a unit derived from an acid monomer containing one or more carboxyl or sulphonyl groups, or alternatively A and B can denote groups derived from zwitterionic carboxybetaine monomer, A and B can also denote a cationic polymer chain containing secondary or tertiary amine groups or quaternary ammonium groups, in which chain at least one of the amine groups carries a carboxyl or sulphonyl group joined via a hydrocarbon radical, or alternatively A and B form part of a chain of a polymer with alpha, beta-dicarboxyethylene units, in which one of the carboxyl groups has been reacted with a polyamine containing one or more primary or secondary amine groups, and at least one cationic polymer of the polyamine or poly-(quaternary ammonium) type, containing amine or ammonium groups in the polymer chain or joined to the latter.

17 Claims, No Drawings

COMPOSITION FOR THE TREATMENT OF KERATIN FIBERS, BASED ON AMPHOTERIC POLYMERS AND CATIONIC POLYMERS

This is a continuation of application Ser. No. 07/877,371, filed May 29, 1992, which is a continuation of application Ser. No. 07/623,084, filed Dec. 6, 1990, abandoned, which is a continuation of application Ser. No. 07/498,490, filed Mar. 26, 1990, now U.S. Pat. No. 4,996,059, which is a continuation of Ser. No. 517,565, filed Jul. 28, 1983, abandoned, which is a continuation of Ser. No. 210,620, filed Nov. 26, 1980, abandoned.

The present invention related to compositions, in particular cosmetic compositions, which are intended for use in the treatment of keratin fibres and in particular hair.

Cationic polymers have already been recommended for use in hair-treatment compositions, in particular for making the hair easier to comb out and imparting softness and suppleness thereto.

However, these cationic polymers, which are characterised by their substantivity, exhibit the disadvantage that they do not impart sufficient hold and gloss to the hair.

To overcome this disadvantage, it has already been proposed to use anionic polymers with the cationic polymers. An association of this type is described, in particular, in French Patent 2,383,660.

However, we have found that, although the association of an anionic polymer and a cationic polymer makes it possible to impart remarkable cosmetic properties to the hair, some disadvantages, such as difficult combing-out, roughness, covering and, in certain cases, static electricity, can nevertheless appear after several successive applications to particularly damaged hair.

We have now discovered, according to the present invention, that, by using an amphoteric polymer in place of the anionic polymers, even particularly damaged keratin fibres, when treated several times with such compositions, comb out very well and exhibit a good hold with time, without roughness or covering, whilst at the same time being supple, soft and uncharged with static electricity and having more body and bulk.

It has been possible to observe particularly valuable results for treatments usually followed by rinsing, such as shampoo treatments and treatments with lotions or creams which are used to obtain a conditioning effect on the hair and are applied before or after colouring, bleaching, shampooing or perming.

We have discovered that hair treated in this way is softer and more silky after several treatments than hair treated with a combination of anionic polymers and cationic polymers.

Accordingly the present invention provides a composition intended for use in the treatment of keratin fibres, which contains at least one cationic polymer and at least one amphoteric polymer, as defined below, as well as a process for the treatment of keratin fibres, using a cationic polymer and an amphoteric polymer; in particular it is a process for attaching amphoteric polymers to keratin fibres by means of a cationic polymer.

The compositions according to the present invention are essentially characterised in that they comprise, in a suitable medium:

a) at least one amphoteric polymer containing units A and B randomly distributed in the polymer chain, where A denotes a unit derived from a monomer containing at least one basic nitrogen atom and B denotes a unit derived from an acid monomer containing one or more carboxyl or sulphonyl groups, or alternatively A and B can denote groups derived from zwitterionic carboxybetaine monomers, A and B can also denote a cationic polymer chain containing secondary or tertiary amine groups or quaternary ammonium groups, in which chain at least one of the amine groups carries a carboxyl or sulphonyl group joined via a hydrocarbon radical, or alternatively A and B form part of a chain of a polymer with alpha, beta-dicarboxyethylene units, in which one of the carboxyl groups has been reacted with a polyamine containing one or more primary or secondary amine groups, and b) at least one cationic polymer of the polyamine or poly-(quaternary ammonium) type, containing amine or ammonium groups in the polymer chain or joined to the latter.

The amphoteric and cationic polymers used according to the invention generally have a molecular weight of 500 to 2 million.

The amphoteric polymers, corresponding to this definition, which are more particularly preferred are chosen from amongst the following polymers:

(1) the polymers resulting from the copolymerisation of a vinyl monomer carrying a carboxyl group, such as acrylic acid, methacrylic acid, maleic acid or alpha-chloro-acrylic acid, and a basic monomer which is a substituted vinyl compound containing at least one basic nitrogen atom, such as dialkylaminoalkyl methacrylates and acrylates and dialkylaminoalkyl methacrylamides and -acrylamides. Products of this type are described in U.S. Pat. No. 3,836,537.

(2) the polymers containing units derived from
   a) at least one monomer chosen from amongst acrylamides or methacrylamides subsituted on the nitrogen by an alkyl radical,
   b) at least one acid comonomer containing one or more reactive carboxyl groups, and
   c) at least one basic comonomer, such as esters, with primary, secondary and tertiary amine substituents and quaternary ammonium substituents, of acrylic and methacrylic acids, and the product resulting from the quaternisation of dimethylaminoethyl methacrylate with dimethyl or diethyl sulphate.

The N-substituted acrylamides or methacrylamides which are more particularly preferred are the groups in which the alkyl radicals contain from 2 to 12 carbon atoms, especially N-ethylacrylamide, N-tert.-butylacrylamide, N-tert.-octyl-acrylamide, N-octylacrylamide, N-decylacrylamide and N-dodecylacrylamide and also the corresponding methacrylamides. The acid comonomers are chosen more particularly from amongst acrylic, methacrylic, crotonic, itaconic, maleic and fumaric acids and also the alkyl monoesters of maleic acid or fumaric acid in which alkyl has 1 to 4 carbon atoms.

The preferred basic comonomers are aminoethyl, butylaminoethyl, N,N'-dimethylaminoethyl and N-tert.-butylaminoethyl methacrylates.

(3) the crosslinked and alkylated polyaminoamides partially or totally derived from polyaminoamides of the general formula:

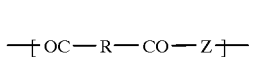

(I)

in which R represents a divalent radical derived from a saturated dicarboxylic acid, from a monocarboxylic or dicarboxylic aliphatic acid with an ethylenic double bond, or from an ester of a lower alkanol having 1 to 6 carbon atoms and of these acids or of a radical derived from the addition of any one of the said acids onto a bis-primary or bis-secondary amine, and Z denotes a radical of a bis-primary or mono- or bis-secondary polyalkylene-polyamine, and preferably represents:

1) in proportions of 60 to 100 mol %, the radical

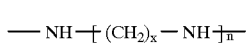
(II)

in which x=2 and n=2 or 3 or alternatively x=3 and n=2, this radical being derived from diethylenetriamine, triethylenetetramine or dipropylenetriamine;

2) in proportions of 0 to 40 mol %, the above radical (II) in which x=2 and n=1 and which is derived from ethylenediamine, or the radical

derived from piperazine; and 3) in proportions of 0 to 20 mol %, the radical —NH—$(CH_2)_6$—NH—, derived from hexamethylenediamine, these polyaminoamides being crosslinked by the addition of a difunctional crosslinking agent chosen from amongst epihalogenohydrins, diepoxides, dianhydrides and bis-unsaturated derivatives, using 0.025 to 0.35 mol of crosslinking agent per amine group of the polyaminoamide, and being alkylated by reaction with acrylic acid, chloroacetic acid or an alkane-sultone or their salts.

The saturated carboxylic acids are preferably chosen from amongst acids having 6 to 10 carbon atoms, such as adipic acid, 2,2,4- and 2,4,4-trimethyl-adipic acids, terephthalic acid and acids with an ethylenic double bond, such as, acrylic, methacrylic and itaconic acids.

The alkane-sultones used in the alkylation are preferably propane- or butane-sultone, and the salts of the alkylating agents are preferably the sodium or potassium salts.

(4) the polymers containing zwitterionic units of the formula:

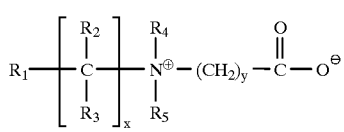
(III)

in which $R_1$ denotes a polymerisable unsaturated group, such as an acrylate, methacrylate, acrylamide or methacrylamide group, x and y independently represent an integer from 1 to 3, $R_2$ and $R_3$ independently represent hydrogen, methyl, ethyl or propyl, and $R_4$ and $R_5$ independently represent a hydrogen atom or an alkyl radical such that the sum of the carbon atoms in $R_4$ and $R_5$ does not exceed 10.

The polymers containing units of this type can also contain units derived from non-zwitterionic monomers, such as vinylpyrrolidone, dimethylaminoethyl or diethylaminoethyl acrylate or methacrylate or alkyl acrylates or methacrylates, acrylamides or methacrylamides, or vinyl acetate.

(5) the polymers derived from chitosan and containing monomer units corresponding to the following formulae:

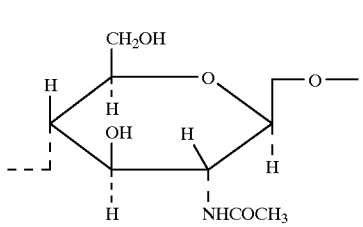
(A)

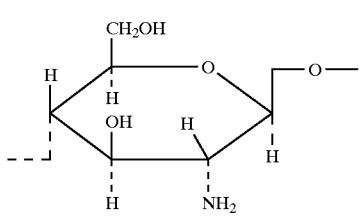
(B)

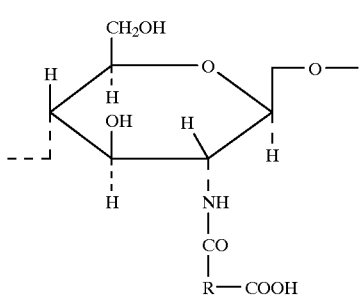
(C)

in which the unit A is present in proportions of 0 to 30%, B is present in proportions of 5 to 50% and C is present in proportions of 30 to 90%. In the formula C, R represents a radical of the formula;

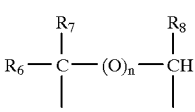

in which, if n=0, $R_6$, $R_7$ and $R_8$, which are identical or different, each represent a hydrogen atom, a methyl, hydroxyl, acetoxy or amino radical, a monoalkylamine radical or a dialkylamino radical, which is optionally interrupted by one or more nitrogen atoms and/or optionally substituted by one or more amine, hydroxyl, carboxyl, alkylthio or sulphonyl groups, or an alkylthio radical in which the alkyl group carries an amino radical, at least one of the radicals $R_6$, $R_7$ and $R_8$ in this case being a hydrogen atom, or, if n is equal to 1, $R_6$, $R_7$ and $R_8$ each represent a hydrogen atom. The salts formed by these compounds with bases or acids are also included.

(6) the polymers corresponding to the general formula IV and described in French Patent 1,400,366:

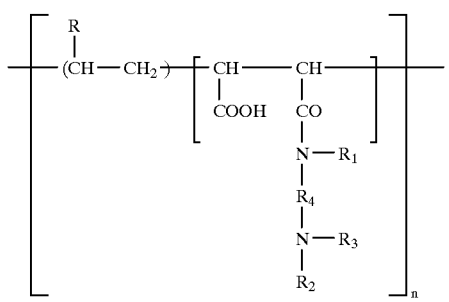 (IV)

in which R represents a hydrogen atom or a $CH_3O$, $CH_3CH_2O$ or phenyl radical, $R_1$ denotes hydrogen or a lower alkyl radical, such as methyl or ethyl, $R_2$ denotes hydrogen or a lower alkyl radical, such as methyl or ethyl, $R_3$ denotes a lower alkyl radical, such as methyl or ethyl, or a radical corresponding to the formula: $R_4$—$N(R_2)_2$, and $R_4$ represents a group —$CH_2$—$CH_2$—, —$CH_2$—$CH_2$—$CH_2$ or

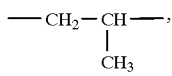

and also the higher homologues of these radicals containing up to 6 carbon atoms.

(7) amphoteric polymers of the type —A—Z—A—Z—, chosen from amongst:

a) the polymers obtained by reacting chloroacetic acid or sodium chloroacetate with compounds containing at least one unit of the formula:

—A—Z—A—Z—A—     (V)

in which A denotes a radical

and in which Z denotes the symbol B or B', and B and B', which are identical or different, denote a divalent radical which is an alkylene radical with a linear or branched chain, which contains up to 7 carbon atoms in the main chain, is unsubstituted or substituted by one or more hydroxyl groups and can also contain oxygen, nitrogen and sulphur atoms and 1 to 3 aromatic and/or heterocyclic rings, the oxygen, nitrogen and sulphur atoms being present in the form of ether, thioether, sulphoxide, sulphone, sulphonium, alkylamino or alkenylamino groups or hydroxyl, benzylamine, amine oxide, quaternary ammonium, amide, imide, alcohol, ester and/or urethane groups; and b) the polymers of the formula:

—A—Z—A—Z—     (V)

in which A denotes a radical

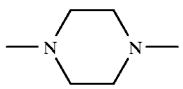

and in which Z denotes B or B' but denotes B' at least once, B having the meaning indicated above and B' being a divalent radical which is an alkylene radical with a linear or branched chain, which has up to 7 carbon atoms in the main chain, is unsubstituted or substituted by one or more hydroxyl radicals and contains one or more nitrogen atoms, the nitrogen atom being substituted by an alkyl chain which is optionally interrupted by an oxygen atom and obligatorily contains one or more hydroxyl and/or carboxyl groups, and also the quaternary ammonium salts resulting from the reaction of chloroacetic acid or sodium chloroacetate with the polymers (V). The preferred amphoteric polymers are those of groups (1), (2), (4), (5) and (6) defined above.

The cationic polymers which are more particularly preferred according to the invention are, in particular:

1) vinylpyrrolidone/aminoalcohol acrylate or methacrylate copolymers (quaternised or unquaternised), such as those sold under the name Gafquat by the Gaf Corp., for example "copolymer 845" and "Gafquat 734 or 755", which are described in greater detail, in particular, in French Patent 2,077,143.

2) cellulose ether derivatives containing quaternary ammonium groups, such as those described in French Patent 1,492,597 and, in particular, the polymers sold under the name JR, such as JR 125, JR 400 and JR 30 M, and the name LR, such as LR 400 and LR 30 M, by Union Carbide Corp., and cationic cellulose derivatives, such as CELQUAT L 200 and CELQUAT H60 sold by National Starch.

3) quaternised guar gum derivatives, such as Jaguar C. 13 S sold by Celanese.

4) cationic polymers chosen from the group comprising:

a) the polymers of the formula:

—A—Z—A—Z—     (VI)

in which A denotes a radical containing two functional amine groups, and preferably

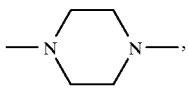

and Z denotes the symbol B or B'; B and B', which are identical or different, denote a divalent radical which is an alkylene radical with a linear or branched chain, which contains up to 7 carbon atoms in the main chain, is unsubstituted or substituted by hydroxyl groups and can also contain oxygen, nitrogen and sulphur atoms and 1 to 3 aromatic and/or heterocyclic rings, the oxygen, nitrogen and sulphur atoms being present in the form of ether or thioether, sulphoxide, sulphone, sulphonium amino, alkylamino, alkenylamino, benzylamino, amine oxide, quaternary ammonium, amide, imide, alcohol, ester and/or urethane groups; these polymers and the process for their preparation are described in French Patent 2,162,025;

b) the polymers of the formula:

—A—$Z_1$—A—$Z_1$—     (VII)

in which A denotes a radical containing two terminal amine groups, and preferably

and $Z_1$ denotes the symbol B or $B'_1$ and denotes the symbol $B'_1$ at least once; $B_1$ denotes a divalent radical which is an alkylene or hydroxyalkylene radical with a linear or branched chain, which has up to 7 carbon atoms in the main chain, and $B'_1$ is a divalent radical which is an alkylene radical with a linear or branched chain, which has up to 7 carbon atoms in the main chain, is unsubstituted or substituted by one or more hydroxyl radicals and is interrupted by one or more nitrogen atoms, the nitrogen atom being substituted by an alkyl has from 1 to 4 carbon atoms, and preferably 4 carbon atoms, is optionally interrupted by an oxygen atom and optionally contains one or more hydroxyl groups; and c) the products resulting from the alkylation, with alkyl and benzyl halides and lower alkyl tosylates or mesvlates of the polymers of the formulae (VI) and (VII), indicated above under a) and b), and the products resulting from the oxidation of the said polymers.

The polymers of the formula (VII) and the process for their preparation are described in French Patent Application 2,280,361.

5) crosslinked and optionally alkylated polyamino-amides chosen from the group comprising at least one water-soluble crosslinked polymer obtained by crosslinking a polyamino-polyamide (A) prepared by the polycondensation of an acid compound with a polyamine. The acid compound is chosen from amongst: (i) organic dicarboxylic acids, (ii) monocarboxylic and dicarboxylic aliphatic acids with an ethylenic double bond, (iii) the esters of the abovementioned acids, preferably the esters of lower alkanols(having from 1 to 6 carbon atoms), and (iv) mixtures of these compounds. The polyamine is chosen from amongst bis-primary and mono- or bis-secondary poly-alkylene-polyamines. Up to 40 mol % of this polyamine can be replaced by a bis-primary amine, preferably ethylenediamine, or by a bis-secondary amine, preferably piperazine, and up to 20 mol % can be replaced by hexa-methylenediamine. The crosslinking is carried out by means of a crosslinking agent (B) chosen from amongst epihalogenohydrins, diepoxides, dianhydrides, unsaturated anhydrides and bis-unsaturated derivatives, and is characterised in that it is carried out using 0.025 to 0.35 mol of crosslinking agent per amine group of the polyamino-polyamide (A). These polymers and their preparation are described in greater detail in French Patent Application No. 2,252,840.

This crosslinked polymer is perfectly soluble in water at a concentration of 10%, without forming a gel, and the viscosity of a 10% strength solution in water at 25° C. is at least 3 centipoises and usually 3 to 200 centipoises.

The alkylation; if appropriate, is carried out with glycidol, ethylene oxide, propylene oxide or acrylamide.

The crosslinked and optionally alkylated polyaminoamides do not contain a reactive group, do not have alkylating properties and are chemically stable.

The polyaminoamides (A) themselves can also be used according to the invention.

6) the water-soluble crosslinked polyaminoamides obtained by crosslinking a polyaminoamide (A, described above) by means of a crosslinking agent chosen from the group comprising:
(I) compounds chosen from the group comprising (1) bis-halogenohydrins, (2) bis-azetidinium compounds, (3) bis-halogenoacyldiamines and (4) alkylene dihalides,
(II) the oligomers obtained by reacting a compound (a), chosen from the group comprising (1) bis-halogenohydrins, (2) bis-azetidinium compounds (3) bis-halogenoacyldiamines, (4) bis-(alkyl halides), (5) epi-halogenohydrins, (6) diepoxides and (7) bis-unsaturated derivatives, with a compound (b), a difunctional compound which is reactive towards the compound (a); and
(III) the product resulting from the quaternisation of a compound chosen from the group comprising the compounds(a) and the oligomers (II) and containing one or more tertiary amine groups which can be totally or partially alkylated, with an alkylating agent (c), preferably chosen from the group comprising methyl or ethyl chlorides, bromides, iodides, sulphates, mesylates and tosylates, benzyl chloride or bromide, ethylene oxide, propylene oxide and glycidol, the crosslinking being carried out using 0.025 to 0.35 mol, in particular 0.025 to 0.2 mol and more particularly 0.025 to 0.1 mol. of crosslinking agent per amine group of the polyaminoamide.

These crosslinking agents and these polymers and also the process for their preparation are described in French Application 2,368,508, the disclosure of which is hereby incorporated by reference.

7) the water-soluble polyaminoamide derivatives resulting from the condensation of a polyalkylene-polyamine with a polycarboxylic acid, followed by alkylation with a difunctional agent, such as adipic acid/dialkylaminohydroxyalkyl-dialkylenetriamine copolymers in which the alkyl radical contains 1 to 4 carbon atoms and preferably denotes methyl, ethyl or propyl, the said copolymers being described in French Patent 1,583,363.

Compounds which make it possible to obtain particularly valuable results are the adipic acid/dimethylaminohydroxypropyl-diethylenetriamine copolymers sold under the name Cartaretine F, F4 or F8 by SANDOZ.

8) the polymers obtained by reacting a poly-alkylene-polyamine containing two primary amine groups and at least one secondary amine group, with a dicarboxylic acid chosen from diglycolic acid and saturated aliphatic dicarboxylic acids having 5 to 8 carbon atoms, the molar ratio of the polyalkylene-polyamine to the dicarboxylic acid being 0.8:1 to 1.4:1, and the resulting polyamide being reacted with epichlorohydrin in a molar ratio of epichlorohydrin to the secondary amine groups of the polyamide of between 0.5:1 to 1.8:1; these polymers are mentioned in U.S. Pat. Nos. 3,227,615 and 2,961,347, which are hereby incorporated by way of reference.

Particularly valuable polymers are that sold under the name HERCOSETT 57 by HERCULES Incorporated and having a viscosity of 30 cps at 25° C. in 10% strength aqueous solution, and that sold under the name PD 170 or DELSETTE 101 by HERCULES, an adipic acid/epoxypropyl-diethylenetriamine copolymer.

9) water-soluble cyclic polymers having a molecular weight of 20,000 to 3,000,000 such as the homopolymers containing, as the main constituent of the chain, units corresponding to the formula (VIII) or (VIII'):

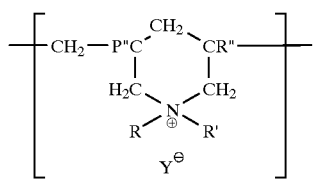
(VIII)

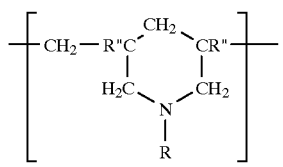
(VIII')

in which formulae R" denotes hydrogen or methyl, R and R' independently of one another denote an alkyl group having from 1 to 22 carbon atoms, a hydroxyalkyl group in which the alkyl group preferably has 1 to 5 carbon atoms, or a lower amidoalkyl group, or R and R' denote, conjointly with the nitrogen atom to which they are attached, heterocyclic groups such as piperidinyl or morpholinyl, and $Y^-$ is an anion, such as bromide, chloride, acetate, borate, citrate, tartrate, bisulphate, bisulphite, sulphate or phosphate, and also the copolymers containing units of the formula. VIII or VIII' and, preferably, derivatives of acrylamide or of diacetone-acrylamide.

Amongst these quaternary ammonium polymers, those which are more particularly preferred are the dimethyldiallylammonium chloride homopolymer sold under the name MERQUAT 100 and having a molecular weight of less than 100,000, and the dimethyl-diallylammonium chloride/acrylamide copolymer having a molecular weight of more than 500,000 and sold under the name MERQUAT 550, by MERCK.

These polymers are described in French Patent 2,080,759 and its Certificate of Addition No. 2,190,406.

10) the poly-(quaternary ammonium) compounds of the formula:

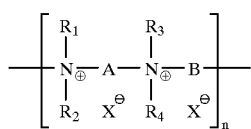
(IX)

in which $R_1$, $R_2$, $R_3$ and $R_4$, which are identical or different, represent aliphatic, alicyclic or arylaliphatic radicals containing a maximum of 20 carbon atoms, or lower hydroxyaliphatic radicals, or alternatively $R_1$ and $R_2$, and $R_3$ and $R_4$, together or separately constitute, with the nitrogen atoms to which they are attached, heterocyclic rings which optionally contain a second hetero-atom other than nitrogen, or alternatively $R_1$, $R_2$, $R_3$ and $R_4$ represent a group

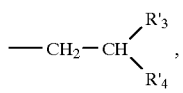

in which $R'_3$ denotes hydrogen or lower alkyl and $R'_4$ denotes —CN, or a group

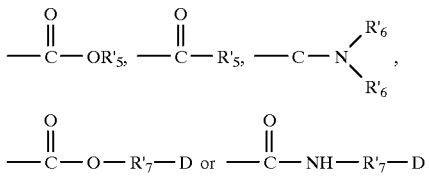

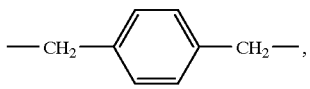

$R'_5$ denoting lower alkyl, $R'_6$ denoting hydrogen or lower alkyl, $R'_7$ denoting alkylene and D denoting a quaternary ammonium group. A and B independently represent polymethylene groups containing from 2 to 20 carbon atoms, which can be linear or branched and saturated or unsaturated and can contain, intercalated in the main chain, one or more aromatic rings, such as the group

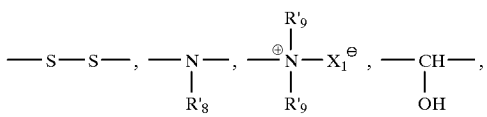

or one or more groups —$CH_2$—Y—$CH_2$—, in which Y denotes O, S, SO, $SO_2$,

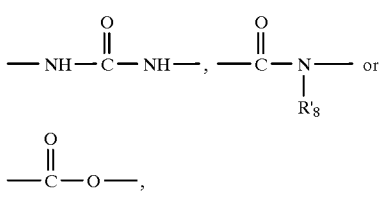

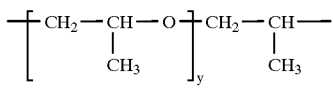

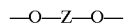

in which $X_1^{\ominus}$ denotes an anion derived from a mineral or organic acid, $R'_8$ denotes hydrogen or lower alkyl and $R'_9$ denotes lower alkyl, or alternatively A, $R_1$ and $R_3$ form a piperazine ring together with the two nitrogens to which they are attached; moreover, if A denotes a linear or branched, saturated or unsaturated aliphatic or hydroxyaliphatic radical, B can also denote a group: —$(CH_2)_n$CO—D—OC—$(CH_2)_n$, in which D denotes a) a glycol residue of the formula:

—O—Z—O— in which Z denotes a linear or branched hydrocarbon radical or a group corresponding to the formulae:

$$\left[\begin{array}{c} CH_2-CH-O \\ | \\ CH_3 \end{array}\right]_y CH_2-CH- \\ | \\ CH_3$$

in which x and y independently denote an integer from 1 to 4, in an individual compound, or any number from 1 to 4, representing an average degree of polymerisation for a mixture of compounds;

b) a bis-secondary diamine residue, such as a piperazine derivative of the formula:

c) a bis-primary diamine residue of the formula:

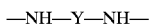

in which Y denotes a linear or branched hydrocarbon radical or the divalent radical $-CH_2-CH_2-S-S-CH_2-CH_2-$; or d) a ureylene group of the formula $-NH-CO-NH-$, n is such that the molecular weight is 1,000 to 100,000.

$X^{\ominus}$ denotes an anion.

Polymers of this type are described, in particular, in French Patents 2,320,330 and 2,270,846, French Applications 76/20,261 and 2,336,434 and U.S. Pat. Nos. 2,273,780, 2,375,853, 2,388,614, 2,454,547, 3,206,462, 2,261,002 and 2,271,378, which are hereby incorporated by reference.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020, which are hereby incorporated by reference.

11) homopolymers or copolymers derived from acrylic or methacrylic acid and containing the unit:

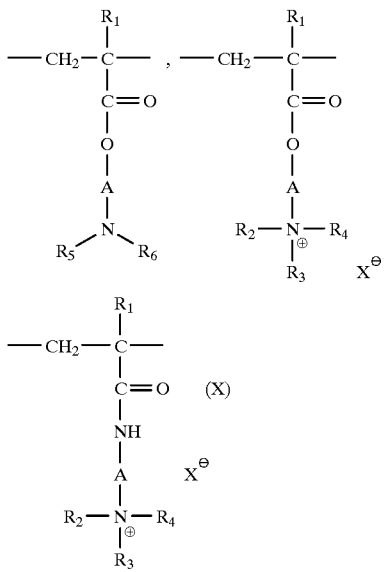

in which $R_1$ is H or $CH_3$, A is a linear or branched alkyl group having 1 to 6 carbon atoms or a hydroxyalkyl group having 1 to 4 carbon atoms, $R_2$, $R_3$ and $R_4$, which are identical or different, are an alkyl group having 1 to 18 carbon atoms or a benzyl group, $R_5$ and $R_6$ are H or alkyl having 1 to 6 carbon atoms, and X denotes metho-sulphate or halogen, such as chlorine or bromine.

The comonomer or comonomers which can be used include acrylamide, methacryl-amide, diacetone-acrylamide, acrylamide and methacrylamide substituted on the nitrogen by lower alkyl, alkyl esters of acrylic and methacrylic acids, vinylpyrrolidone and vinyl esters.

Examples which may be mentioned are:

the acrylamide/beta-methacryloyloxyethyltrimethyl-ammoniummethosulphatecopolymers sold under the names Reten 205, 210, 220 and 240 by Hercules, the ethyl methacrylate/oleyl methacrylate/beta-methacryloyloxydiethylmethylammonium methosulphate copolymers classified under the name Quaternium 38 in the Cosmetic Ingredient Dictionary, the ethyl methacrylate/abietyl methacrylate/beta-methacryloyloxydiethylmethylammonium methosulphate copolymer classified under the name Quaternium 37 in the Cosmetic Ingredient Dictionary, the beta-methacryloyloxyethyltrimethylammonium bromide polymer classified under the name Quaternium 49 in the Cosmetic Ingredient Dictionary, the beta-methacryloyloxyethylmethylammonium methosulphate/beta-methacryloyloxystearyldimethyl-ammonium methosulphate copolymer classified under the name Quaternium 42 in the Cosmetic Ingredient Dictionary, the copolymer of (aminoethyl acrylate) phosphate and (aminoethyl acrylate) acrylate sold under the name Catrex by National Strach and having a viscosity of 700 cps at 25° C. in an 18% strength aqueous solution, and the crosslinked graft cationic copolymers having a molecular weight of 10,000 to 1,000,000, and preferably 15,000 to 500,000, and resulting from the copolymerisation of:

a) at least one cosmetic monomer, b) dimethylaminoethyl methacrylate, c) polyethylene glycol and d) a polyunsaturated crosslinking agent, which copolymers are described in French Patent 2,189,434, which is hereby incorporated by reference.

The crosslinking agent is taken from the group ethylene glycol dimethacrylate, a diallyl phthalate, divinylbenzene., tetraallyloxyethane, or. polyallylsucrose having from 2 to 5 allyl groups per molecule of sucrose.

The cosmetic monomer can be of a very varied type, for example a vinyl ester of an acid having from 2 to 18 carbon atoms, an allyl or methallyl ester of an acid having from 2 to 18 carbon atoms, an acrylate or methacrylate of a saturated alcohol having from 1 to 18 carbon atoms, an alkyl vinyl ether in which the alkyl radical has from 2 to 18 carbon atoms, an olefine having from 4 to 18 carbon atoms, a vinyl heterocyclic derivative, a dialkyl or N,N-dialkylaminoalkyl maleate in which the alkyl radicals have from 1 to 3 carbon atoms, or an anhydride of an unsaturated acid.

The polyethylene glycol has a molecular weight of 200 to several million and preferably 300 to 30,000.

These crosslinked graft copolymers preferably consist of:

a) 3 to 95% by weight of at least one cosmetic monomer chosen from the group comprising vinyl acetate, vinyl propionate, methyl methacrylate, stearyl methacrylate, lauryl methacrylate, ethyl vinyl ether, cetyl vinyl ether, stearyl vinyl ether, hex-1-ene, octadec-1-ene, N-vinylpyrrolidone, mono-N,N-diethylamino-ethyl maleate, maleic anhydride and diethyl maleate, b) 3 to 95% by weight of dimethylaminoethyl methacrylate, c) 2 to 50% by weight, and preferably 5 to 30%, of polyethylene glycol, and d) 0.01 to 8% by weight of a crosslinking agent as defined above, the percentage of the crosslinking agent being expressed relative to the total weight of a)+b)+c).

Other cationic polymers which can be used include polyalkyleneimines and in particular polyethyleneimines, polymers containing vinylpyridine or vinylpyridinium units in the chain, products resulting from the condensation of polyamines and epichlorohydrin, quaternary polyureylenes, and chitosan derivatives.

The preferred compositions for the purpose of the present invention are compositions containing, as the amphoteric polymer, a crosslinked and alkylated polyaminoamide as defined in group (3) of the amphoteric polymers described above, and, as the cationic polymer, crosslinked and optionally alkylated polyaminoamides or the polyaminoamide derivatives as defined in groups (5), (6), (7), (9) and (10) of the cationic polymers described above.

Another composition giving particularly advantageous results comprises polymers containing units derived from at least one monomer chosen from acrylamides or methacrylamides substituted on the nitrogen by an alkyl radical, and derived from at least one acid comonomer containing one or more reactive carboxyl groups, as defined in group (2) of the amphoteric polymers, the cyclopolymers and the poly-(quaternary ammonium) compounds of groups (9) and (10) of the cationic polymers.

Amongst these compositions those giving particularly notable results are those comprising the amphoteric polymer referred to as PAM-2, with the cationic polymer PAA-1 or Cartaretine F4, or alternatively the amphoteric polymer sold under the name AMPHOMER, with the cationic polymers referred to as PAQ-1 or PAQ-3.

The polymers used according to the invention are typically present in the compositions in proportions from 0.01 to 10% by weight and preferably from 0.5 to 5% by weight. The pH of these compositions is generally from 2 to 11, especially from 3 to 10 and preferably from 4 to 8.5.

The compositions according to the invention preferably do not contain other polymers and in particular do not contain an anionic polymer.

These compositions can be presented in various forms, such as a liquid, a cream, an emulsion or a gel. In addition to water, they can contain any cosmetically acceptable solvent chosen, in particular, from amongst monoalcohols, such as alkanols having 1 to 8 carbon atoms, for example ethanol and isopropanol, benzyl alcohol and phenylethyl alcohol, and polyalcohols, such as alkylene glycols, for example ethylene glycol and propylene glycol, and glycol ethers, such as mono-, di- and tri-ethylene glycol monoalkyl ethers, for example ethylene glycol monomethyl ether, ethylene glycol monoethyl ether and diethylene glycol monoethyl ether, used singly or in a mixture. These solvents are generally present in proportions which are less than or equal to 70% by weight, relative to the weight of the total composition.

These compositions can also contain electrolytes and, amongst these, those which are more particularly preferred are alkali metal salts, such as the sodium, potassium or lithium salts. These salts are preferably halides, such as the chloride or bromide, sulphates, or the salts of organic acids, such as the acetate or lactates.

These compositions can also be in the form of a powder to be diluted before use.

Those compositions of which the usual applications are followed by rinsing are preferred and give the most surprising results.

In particular, they can be in the form of a shampoo, a rinsing lotion, a cream or a treating product, which can be applied before or after colouring or bleaching, before or after shampooing or before or after perming, and they can also take the form of colouring products, wavesetting lotions, brushing lotions and bleaching, perming and straightening products.

A preferred embodiment is one in which the composition is in the form of a shampoo. In this case, in addition to the abovementioned polymers, the compositions according to the invention contain at least one anionic non-ionic, cationic or amphoteric surface-active agent or mixtures thereof.

Amongst the anionic surface-active agents, there may be mentioned, in particular, the following compounds and also mixtures thereof: the alkali metal salts, the ammonium salts, the amine salts or the aminoalcohol salts of the following compounds: alkyl-sulphates, alkyl-ether-sulphates, alkylamide-sulphates and alkylamide-ether-sulphates, alkylaryl-polyether-sulphates and monoglyceride-sulphates; alkylsulphonates, alkylamidesulphonates, alkylarylsulphonates and alpha-olefine-sulphonates; alkylsulphosuccinates, alkyl-ether-sulphosuccinates and alkylamide-sulphosuccinates; alkyl-sulphosuccinamates; alkyl-sulphoacetates and alkyl-polyglycerol-carboxylates; alkyl-phosphates and alkyl-ether-phosphates; alkyl-sarcosinates, alkylpolypeptidates, alkylamidopolypeptidates, alkyl-isethionates and alkyltaurates, the alkyl radical in all these compounds being a linear chain having 12 to 18 carbon atoms, and fatty acids, such as oleic acid, ricinoleic acid, palmitic acid, stearic acid, acids derived from copra oil or from hydrogenated copra oil, and carboxylic acids of polyglycol ethers, corresponding to the formula:

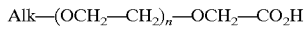

$$Alk—(OCH_2—CH_2)_n—OCH_2—CO_2H$$

in which the substituent Alk corresponds to a linear chain having from 12 to 18 carbon atoms and in which n is an integer from 5 to 15.

Amongst the anionic surface-active agents, those which are more particularly preferred are: sodium lauryl-sulphate, ammonium lauryl-sulphate or triethanol-amine laurylsulphate, the sodium salt of sulphated lauryl alcohol oxyethyleneated with, say, 2.2 mols of ethylene oxide, the triethanolamine salt of lauroyl-keratinic acid, the triethanolamine salt of the product resulting from the condensation of copra acids and animal protein hydrolysates, and the products of the formula:

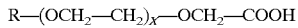

$$R—(OCH_2—CH_2)_x—OCH_2—COOH$$

in which R is generally a $C_{12}$ to $C_{14}$ alkyl radical and x varies from 6 to 10.

Amongst the non-ionic surface-active agents which can optionally be used in a mixture with the above-mentioned anionic surface-active agents, there may be mentioned in particular the products resulting from the condensation of a monoalcohol, an alpha-diol, an alkylphenol, an amide or a diglycolamide with glycidol, such as the products corresponding to the formula:

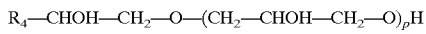

$$R_4—CHOH—CH_2—O—(CH_2—CHOH—CH_2—O)_pH$$

in which $R_4$ denotes an aliphatic, cycloaliphatic or arylaliphatic radical preferably having 7 to 21 carbon atoms, and mixtures thereof, it being possible for the aliphatic chains to contain ether, thioether or hydroxymethylene groups, and in which p represents an average statistical value of 1 to 10 inclusive, as described in French Patent 2,091,516; products corresponding to the formula

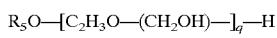

$$R_5O—[C_2H_3O—(CH_2OH)—]_q—H$$

in which $R_5$ denotes an alkyl, alkenyl or alkylaryl radical and q has an average statistical value of 1 to 10, such as the compounds described in French Patent 1,477,048; and products corresponding to the formula:

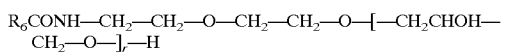

$$R_6CONH—CH_2—CH_2—O—CH_2—CH_2—O—[—CH_2CHOH—CH_2—O—]_r—H$$

in which $R_6$ denotes a saturated or unsaturated, linear or branched aliphatic radical, or a mixture of such radicals, which can optionally contain one or more hydroxyl groups, has 8 to 30 carbon atoms and is of natural or synthetic origin, and r represents an integer or decimal number from 1 to 5 and denotes the average degree of condensation, such as the compounds described in French Patent Specification 2,328, 763.

Other compounds included in this class are polyoxyethyleneated or polyglycerolated alcohols, alkyl-phenols or fatty acids with linear fatty chains containing 8 to 18 carbon atoms. There may also be mentioned copolymers of ethylene oxide and propylene oxide, products resulting from the condensation of ethylene oxide and propylene oxide with fatty alcohols, polyoxyethyleneated fatty amides, polyoxyethyleneated fatty amines, ethanolamides, fatty acid esters of glycol, fatty acid esters of sorbitol and fatty acid esters of sucrose.

Amongst these non-ionic surface-active agents, those which are more particularly preferred correspond to the formula:

$$R_4\text{—CHOH—CH}_2\text{—O—(CH}_2\text{—CHOH—CH}_2\text{—O)}_p\text{—H}$$

in which $R_4$ denotes a mixture of alkyl radicals having 9 to 12 carbon atoms and p has a statistical value of, say, 3.5, to the formula:

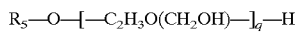

$$R_5\text{—O—[—C}_2\text{H}_3\text{O(CH}_2\text{OH)—]}_q\text{—H}$$

in which $R_5$ denotes $C_{12}H_{25}$ and q has a statistical value of 4 to 5, and to the formula:

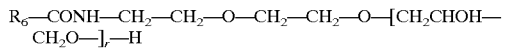

$$R_6\text{—CONH—CH}_2\text{—CH}_2\text{—O—CH}_2\text{—CH}_2\text{—O—[CH}_2\text{CHOH—CH}_2\text{O—]}_r\text{—H}$$

in which $R_6$ denotes a mixture of radicals derived from lauric, myristic, oleic and copra acids and r has a statistical value of 3 to 4.

The preferred polyoxyethyleneated or polyglycerolated fatty alcohols are oxyethyleneated oleyl alcohol containing 10 mols of ethylene oxide, oxyethyleneated lauryl alcohol containing 12 mols of ethylene oxide, oxyethyleneated nonylphenol containing 9 mols of ethylene oxide, polyglycerolated oleyl alcohol containing 4 mols of glycerol and polyoxyethyleneated sorbitan monolaurate containing 20 mols of ethylene oxide.

Amongst the cationic surface-active agents which can be used by themselves or in a mixture, there may be mentioned, in particular, fatty amine salts, such as alkylamine acetates, quaternary ammonium salts, such as alkyldimethylbenzylammonium, alkyltrimethylammonium, alkyldimethylhydroxyethylammonium and dimethyldistearyl-ammonium chlorides and bromides, alkylaminoethyltrimethyl-ammonium methosulphates and alkylpyridinium salts, and imidazoline derivatives. The alkyl radicals in these compounds preferably have 1 to 22 carbon atoms. Compounds of cationic character, such as amine oxides, for example alkyldimethylamine oxides or alkylaminoethyl-dimethylamine oxides, may also be mentioned.

Amongst the amphoteric surface-active agents which can be used, there may be mentioned, more particularly, alkylamino-monopropionates and -dipropriontates, betaines,, such as N-alkylbetaines, N-alkylsulphobetaines and N-alkylaminobetaines, cycloimidinium compounds, such as alkylimidazolines, and asparagine derivatives. The alkyl group in these surface-active agents preferably has 1 to 22 carbon atoms.

In these shampoos, the concentration of surface-active agent is generally 3 to 50% by weight and preferably 3 to 30% and the pH is generally 3 to 10.

Another preferred embodiment is one in which the composition is in the form of a rinsing lotion to be applied mainly before or after shampooing. These lotions are usually aqueous or aqueous-alcoholic solutions, or emulsions, thickened lotions or gels.

If the compositions are presented in the form of emulsions, they can be non-ionic or anionic. The non-ionic emulsions mainly consist of a mixture of an oil and/or a fatty alcohol with a polyoxyethyleneated alcohol, such as polyoxyethyleneated stearyl or cetyl/stearyl alcohols. Cationic surface-active agents, such as those defined above, can be added to these compositions.

The anionic emulsions are essentially made from soap.

If the compositions are presented in the form of thickened lotions or of gels, they contain thickeners in the presence or absence of solvents. The thickeners, which can be used include sodium alginate, gum arabic or cellulose derivatives, such as methylcellulose, hydroxymethylcellulose, hydroxyethylcellulose, hydroxypropylcellulose or hydroxypropylmethylcellulose. It is also possible to thicken the lotions with a mixture of polyethylene glycol and polyethylene glycol stearate or distearate or with a mixture of a phosphoric acid ester and an amide. The concentration of thickener is generally 0.5 to 30% by weight and preferably from 0.5 to 15% by weight. The pH of the rinsing lotions is generally from 3 to 9.

If the compositions according to the invention are presented in the form of styling lotions, shaping lotions or so-called wavesetting lotions, these lotions generally comprise, in aqueous, alcoholic or aqueous-alcoholic solution, the components of the association defined above and also, optionally, non-ionic polymers and anti-foam agents.

If the compositions of the present invention constitute dyeing compositions for keratin fibres, they contain, in addition to the amphoteric polymer (or polymers) and the cationic polymer (or polymers), at least one oxidation dyestuff precursor and/or one direct dyestuff, and optionally various adjuvants which make it possible to present them in the form of a cream, gel or solution described above.

The compositions can also contain antioxidants, sequestering agents or any other adjuvant normally used in this type of composition.

The oxidation dyestuff precursors are aromatic compounds of the diaminobenzene or diaminopyridine, aminophenol or phenol type. These precursors include, on the one hand, the dyestuff precursors of the "para" type and the dyestuff precursors of the "ortho" type, chosen from diaminobenzenes, diaminopyridines, aminophenols and diphenylamines, and, on the other hand, the couplers, which are "meta" derivatives chosen from meta-diaminobenzenes, meta-diaminopyridines, meta-aminophenols, meta-diphenols, phenols and naphthols.

Amongst the direct dyestuffs, there may be mentioned azo dyestuffs, anthraquinone dyestuffs, nitrobenzene derivatives, indamines, indophenols and indoanilines.

The pH of these dyeing compositions is generally 7 to 11, it can be adjusted to the desired value by adding an alkalising agent, such as ammonia, alkali metal hydroxides, alkali metal and ammonium carbonates, alkylamines, alkanolamines or a mixture thereof.

Finally, the association according to the invention can be used in compositions intended for waving or straightening the hair. In addition to the amphoteric polymer (or polymers) and the cationic polymer (or polymers), this composition contains one or more reducing agents and optionally other adjuvants normally used in this type of composition, and it is used conjointly with a neutralising composition.

The reducing agents are typically sulphites and mercaptans and more particularly from amongst thioglycolates or thiolactates or a mixture thereof.

The neutralising composition contains an oxidising agent such as hydrogen peroxide and alkali metal bromates or perborates.

The compositions of this invention can also be pressurised in the form of an aerosol; carbon dioxide, nitrogen, nitrous oxide and volatile hydrocarbons, such as butane, isobutane and propane, or preferably chlorinated or fluorinated hydrocarbons, can be used as the propellent gas.

The compositions according to the invention can contain any other ingredient normally used in cosmetics, such as perfumes, dyestuffs which can serve to colour the composition itself, preservatives, electrolytes, sequestering agents, thickeners, softeners, synergistic agents, foam stabilisers, sun filters and peptising agents, depending on the application envisaged.

The process for the treatment of keratin fibres according to the invention can consist in applying the composition, containing the amphoteric polymer defined above and the cationic polymer defined above, directly to the hair, in particular by shampooing, by colouring the head of hair, by permanently waving the hair or by conditioning the hair using the abovementioned compositions.

The association according to the invention can also be formed in situ on the hair by applying in a first stage, a composition, for example in the form of a pre-lotion, containing the cationic polymer, and in a second stage, a composition, such as a shampoo or a dye composition, containing the amphoteric polymer.

According to another embodiment of the invention, it is possible to apply, in a first stage, a shampoo containing the cationic polymer, and in a second stage, a composition, such as a lotion, containing the amphoteric polymer.

A possible procedure consists in successively using a perming, straightening, colouring or bleaching composition containing the cationic polymer, followed by a composition containing the amphoteric polymer, the latter being present in a composition which can be a shampoo, an oxidising solution or a simple lotion.

Another possible procedure consists in successively using, in a first stage, a first shampoo containing the cationic polymer, and in a second stage, a second shampoo containing the amphoteric polymer, it being possible for the pH values of the compositions applied in these two stages to be different and to be adjusted so that, at the moment of application of the composition containing the amphoteric polymer, the conditions are such that they permit a good deposition of the combination according to the invention, on the hair.

The invention also provides a process for curling or straightening the hair, which consists in applying, in a first stage, a reducing composition containing the cationic polymer/amphoteric polymer combination, and in a second stage, the neutralising composition.

According to a modified embodiment, it is possible to apply, in a first stage, the reducing composition containing the cationic polymer (or polymers), and in a second stage, the neutralising composition containing the amphoteric polymer (or polymers).

The process of the present invention can also be defined as a process for attaching amphoteric polymers to keratin fibres, in which the attachment is caused by associating it with a cationic polymer which is either present in the same composition or has been applied to the keratin fibres beforehand.

The following Examples further illustrate the present invention. Amounts are expressed by weight of active ingredient.

EXAMPLES 1–8

The following composition is prepared:

| | |
|---|---|
| Amphoteric polymer referred to as AZAM-1 | 0.8 g |
| Cationic polymer referred to as ONAMER M | 0.4 g |
| Maypon 4 CT | 8 g |
| Surface-active agent referred to as AES | 1 g |
| Sodium chloride | 3 g |
| Sodium hydroxide q.s.p. | pH 8.7 |
| Water q.s.p. | 100 g |

This composition is used as a shampoo.

The hair is impregnated when dirty and wet and the formation of a mild foam is observed. After rinsing, the hair is easy to comb out when wet.

When dry, the head of hair is characterised by its springiness and, in particular, by its bulk and its hold.

Other Examples (2 to 8) of shampoos according to the invention are illustrated in Table I. As for Example 1, the hair is found to be easy to comb out when wet and, when dry, the hair is springy, bulky and has a good hold.

TABLE I

SHAMPOOS

| Example No. | POLYMER AMPHOTERIC | % | CATIONIC | % | SURFACE-ACTIVE AGENT | % | SOLVENTS and/or ADJUVANTS | % | pH | Acidifying or alkalising agent |
|---|---|---|---|---|---|---|---|---|---|---|
| 2 | AZAM-2 | 0.7 | PAQ-3 | 0.6 | TA-2 Lipoproteol LCO | 8 7 | Sodium chloride | 1 | 8 | Hydrochloric acid |
| 3 | PAM-1 | 0.7 | Kytex H | 0.5 | Miranol C.2M TA-1 | 5 10 | | | 4 | Hydrochloric acid |
| 4 | Amphomer | 0.3 | PAQ-1 | 0.4 | TA-2 | 12 | Sodium chloride | 5 | 5.6 | Hydrochloric acid |
| 5 | Amphomer | 0.4 | Gafquat 755 | 0.2 | TA-1 | 12 | | | 6.3 | Hydrochloric acid |
| 6 | Amphomer | 0.4 | PAA-1 | 0.5 | ELA 12 | 5 | Sodium chloride | 5 | 6 | Hydrochloric |

TABLE I-continued

SHAMPOOS

| Example No. | POLYMER AMPHOTERIC | % | CATIONIC | % | SURFACE-ACTIVE AGENT | % | SOLVENTS and/or ADJUVANTS | % | pH | Acidifying or alkalising agent |
|---|---|---|---|---|---|---|---|---|---|---|
| 7 | Amphomer | 0.3 | PAQ-2 | 0.5 | Miranol C.2M<br>Sandopan DTC.AC | 7<br>8 | Sodium chloride | 4 | 8.5 | acid<br>Sodium hydroxide |
| 8 | Amphomer | 0.2 | Cartaretine F4 | 0.7 | Miranol C.2M<br>Triethanolamine lauryl-sulphate | 4<br>25 | Copra diethanol-amide | 2 | 8 | Lactic acid |

EXAMPLES 9–20

The following composition is prepared:

| | |
|---|---|
| Amphoteric polymer referred to as PAM-3 | 0.4 g |
| Cationic polymer referred to as PAA-R | 0.5 g |
| Non-ionic surface-active agent referred to as TA-1 | 0.5 g |
| Hydrochloric acid q.s.p. | pH 8 |
| Water q.s.p. | 100 g |

This composition is used for rinsing the hair.

This composition is applied to hair which has been washed and towel-dried. After an interval of a few minutes, the hair is rinsed.

The hair is easy to comb out when wet. When dry, the hair is bulky and the style holds well.

Similar results are obtained by applying the compositions of Examples 10 to 20 of Table II, under the same conditions as in Example 9 above.

TABLE II (RINSE-OFF LOTIONS)

| Example No. | POLYMER AMPHOTERIC | % | CATIONIC | % | SURFACE-ACTIVE AGENT | % | SOLVENTS and/or ADJUVANTS | % | pH | Acidifying or alkalising agent |
|---|---|---|---|---|---|---|---|---|---|---|
| 11 | Amphomer | 0.7 | Onamer M | 0.5 | | | Cetyl/stearyl alcohol<br>Polawax GP 200<br>Cellosize QP 4400 H<br>Ammonyx 27 | 2<br>3<br>0.5<br>1.5 | 5.7 | Lactic acid |
| 11 | Amphomer | 0.75 | PAA-1 | 0.6 | | | Lexein X.250 | 0.5 | 8.8 | Hydrochloric acid |
| 12 | PAM-2 | 0.6 | PAQ-3 | 0.8 | | | Cetyl/stearyl alcohol<br>Cellosize QP 4400 H<br>Lexein X.250<br>Ammonyx 27 | 2<br>0.7<br>0.8<br>2 | 5 | Hydrochloric acid |
| 13 | PAM-2 | 2 | Onamer M | 0.9 | | | | | 7 | Lactic acid |
| 14 | PAM-2 | 0.9 | JR 400 | 0.7 | | | | | 4 | Hydrochloric acid |
| 15 | AZAM-1 | 1.5 | Gafquat 755 | 2 | | | | | 3.5 | Hydrochloric acid |
| 16 | AZAM-1 | 0.1 | PAQ-2 | 0.05 | | | Lexein X.250 | 0.1 | 3.5 | Hydrochloric acid |
| 17 | AM | 0.8 | PAQ-3 | 0.46 | | | Lexein X.250 | 1.6 | 5 | Hydrochloric acid |
| 18 | AM | 1.5 | PAA-1 | 0.62 | | | Lexein S.620 | 1.1 | 8.6 | Hydrochloric acid |
| 19 | CHIT | 3 | PAQ-3 | 5 | CSA 15 EO | 3 | Cetyl alcohol<br>Ammonyx 27 | 6<br>2 | 7.3 | Hydrochloric acid |
| 20 | CHIT | 0.06 | JR 400 | 0.15 | | | | | 3.2 | Hydrochloric acid |

On applying the compositions of Examples 17, 18 and 20 in the form of a wavesetting lotion, without rinsing, it is observed that the style holds well and that the hair has a soft feel.

EXAMPLES OF "TWO-STAGE" FORMULATIONS

EXAMPLE 21

An aqueous lotion having the following composition is applied in a first stage:

| | | |
|---|---|---|
| Cartaretine F4 | 0.6 | g |
| Cellosize QP 4400 H | 0.5 | g |
| Water q.s.p. | 100 | g |
| pH 7 | (using HCl) | |

After an interval of a few minutes, an aqueous lotion having the following composition is applied in a second stage:

| | | |
|---|---|---|
| AMPHOMER | 1.2 | g |
| Cellosize QP 4400 H | 0.4 | g |
| Water q.s.p. | 100 | g |
| pH = 8.1 | (using HCl) | |

EXAMPLE 22

A shampoo having the following composition is applied in a first stage:

| | | |
|---|---|---|
| MERQUAT 100 | 0.5 | g |
| Surface-active agent referred to as TA-1 | 9 | g |
| Water q.s.p. | 100 | g |
| pH = 8.6 | (using HCl) | |

An aqueous lotion having the following composition is applied in a second stage:

| | | |
|---|---|---|
| Polymer referred to as PAM-2 | 0.3 | g |
| CELLOSIZE QP 4400 H | 0.4 | g |
| Water q.s.p. | 100 | g |
| pH = 7 | (using HCl) | |

EXAMPLE 23

The following composition A is prepared:

| | | |
|---|---|---|
| PAM-2 | 1.0 | g |
| Neutral ortho-oxyquinoline sulphate | 0.05 | g |
| 70% strength hydrogen peroxide q.s.p. | 20 volumes strength | |
| Hydrochloric acid q.s.p. | pH 2 | |
| Water q.s.p. | 100 | g |

Before use, 40 g of this composition are mixed with 40 g of the following composition B2:

| | | |
|---|---|---|
| Nonylphenol containing 4 mols of ethylene oxide | 19.0 | g |
| Nonylphenol containing 9 mols of ethylene oxide | 17.0 | g |
| Coconut diethanolamide | 14.0 | g |
| Propylene glycol | 10.0 | g |
| Ethyl alcohol | 3.5 | g |
| PAQ-4 | 2.0 | g |
| Ethylenediaminetetraacetic acid | 1.0 | g |
| 22° Be strength ammonia solution | 10 | ml |
| Water q.s.p. | 100 | g |

A creamy gel is obtained. It is applied to deep chestnut hair. After an interval of 30 to 45 minutes, the hair is rinsed.

The hair is then deep blond.

EXAMPLE 24

The following composition A is prepared:

| | | |
|---|---|---|
| PAM-2 | 1.0 | g |
| Neutral ortho-oxyquinoline sulphate | 0.05 | g |
| Hydrogen peroxide q.s.p. | 20 volumes strength | |
| Hydrochloric acid q.s.p. | pH 2 | |
| Water q.s.p. | 100 | g |

Before use, this composition is mixed with the following composition B2:

| | | |
|---|---|---|
| Polyoxyethyleneated nonylphenol containing 4 mols of ethylene oxide | 19.0 | g |
| Polyoxyethyleneated nonylphenol containing 9 mols of ethylene oxide | 17.0 | g |
| PAQ-4 | 2.0 | g |
| Ethyl alcohol | 3.5 | g |
| Propylene glycol | 10.0 | g |
| 22° Be strength ammonia solution | 10 | ml |
| Coconut diethanolamide | 14.0 | g |
| Meta-diaminoanisole sulphate | 0.03 | g |
| Resorcinol | 0.40 | g |
| P-aminophenol | 0.087 | g |
| Nitro-p-phenylenediamine | 100 | g |
| Ethylenediaminetetraacetic acid | 3.0 | g |
| Sodium bisulphite (d = 1.32) | 1.20 | g |
| Water q.s.p. | 100 | g |

50 g of this formulation are mixed with the same amount of composition A, in a bowl, and the resulting gel is applied to the hair with a paintbrush.

After an interval of 30 minutes, the hair is rinsed.

The hair is easy to comb out and has a silky feel. It is set in waves and dried.

The hair is glossy and springy, it has body and volume, it has a silky feel and it is easy to comb out.

On a brown background, a chestnut shade is obtained.

EXAMPLE 25

The following compositions are prepared:

a) Reducing composition

| | | |
|---|---|---|
| Thioglycolic acid | 6.0 | g |
| Ammonia solution q.s.p. | pH 9.5 | |
| Sequestering agent | 0.2 | g |
| MERQUAT 100 | 2.0 | g |
| Perfume | 0.5 | g |
| Water q.s.p. | 100 | ml | b) Neutralising liquid

-continued

| | |
|---|---|
| Potassium bromate | 9.5 g |
| Amphomer | 1.0 g |
| Tartaric acid | pH 6.5 |
| Perfume | |
| Dye stuff | |
| Water q.s.p. | 100 g |

On sensitised hair, the reducing liquid can be applied very easily and penetrates deeply into the hair.

After rinsing and applying the neutralising liquid, a very uniform curl is observed.

After drying, the style holds particularly well.

EXAMPLE 26

The following compositions are prepared:

| a) Reducing composition | |
|---|---|
| Ammonium sulphite | 4.0 g |
| Ammonium bisulphite | 3.3 g |
| Monoethanolamine | 3.9 g |
| Onamer M | 2.0 g |
| Polyoxyethyleneated nonylphenol containing 9 mols of ethylene oxide | 0.5 g |
| Perfume | 0.5 g |
| Water q.s.p. | 100 ml |
| b) Neutralising liquid | |
| Potassium bromate | 9.5 g |
| PAM-2 | 1.0 g |
| Tartaric acid | pH 6.5 |
| Perfume | |
| Dyestuff | |
| Water q.s.p. | 100 g |

On sensitised hair, the reducing liquid can be applied very easily and penetrates deeply into the hair.

After rinsing and applying the neutralising liquid, a very uniform curl is observed.

After drying, the style holds particularly well.

In the above Examples, the tradenames and the abbreviations used denote the following products:

PAM-1: polymer resulting from the reaction of the polymer PAA-1 with propane-sultone in proportions of 50%.

PAA-1: polyaminoamide resulting from the polycondensation of adipic acid and diethylenetriamine in equimolecular amounts and crosslinked with epichlorohydrin at a rate of 11 mols of crosslinking agent per 100 amine groups of the polyaminoamide.

PAM-2: polymer resulting from the alkylation of the polymer PAA-1 with sodium chloroacetate.

AZAM-1: polymer obtained by the polycondensation of epichlorohydrin and piperazine, in the presence of sodium hydroxide, and converted to a betaine.

AZAM-2: mixed product resulting from the polycondensation of epichlorohydrin and a mixture of piperazine+ sodium glycinate in molar proportions of 60/40. Unit of the amphoteric polymer: —A—CH$_2$—CHOH—CH$_2$—in which A denotes either

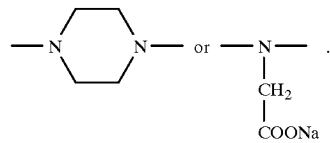

AMPHOMER: octylacrylamide/acrylate/butylaminoethyl methacrylate copolymer sold National Starch.

AM: polymer of the formula:

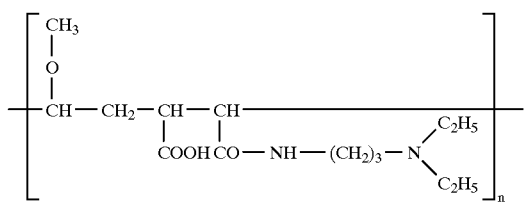

PAM-3: polymer resulting from the alkylation of the polymer PAA-1 with propane-sultone. (100%)

CHIT: polymer containing the units

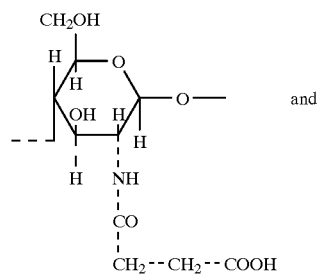

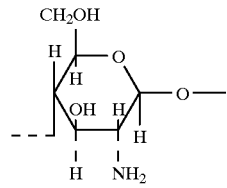

in proportions of about 50/50.

PAA-R: polyaminoamide resulting from the polycondensation of adipic acid and diethylenetriamine in equimolecular amounts and crosslinked with a random oligomeric crosslinking agent of the formula:

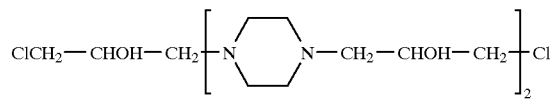

PAQ-1: polymer of the formula:

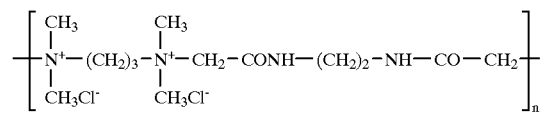

having an absolute viscosity of 1,94 cps

PAQ-2: polymer of the formula:

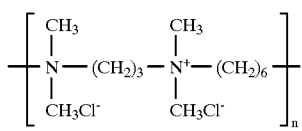

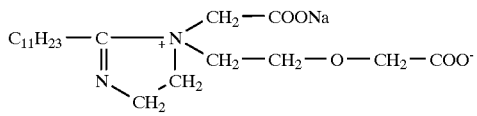

PAQ-3: polymer of the formula:

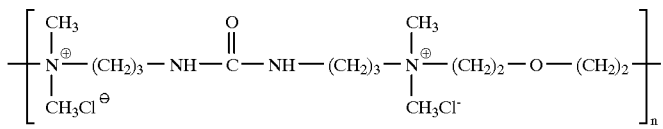

KYTEX H: partially deacetylated chitin sold by the Hercules.
GAFQUAT 755: quaternary polyvinylpyrrolidone copolymer having a molecular weight of 1,000,000 and marketed by General Anilin.
CARTARETINE F4: adipic acid/ dimethylaminohydroxypropyl-diethylenetriamine copolymer sold by Sandoz
ONAMER M: poly-[(dimethylbutenylammonium chloride)-α,ω-(triethanolammonium chloride)] sold by Onyx Chemical Co.
JR 400: polymer of hydroxyethylcellulose and epichlorohydrin, quaternised with trimethylamine and sold by Union Carbide.
MERQUAT 100: dimethyldialkylammonium chloride homopolymer having a molecular weight of less than 100,000 and sold by Merck.
MAYPON 4 CT: triethanolamine salt of the product resulting from the condensation of copra acid and animal protein hydrolysate, sold by Stepan.
AES: sodium salt of a sulphated alcohol($C_{12}$–$C_{14}$) oxyethyleneated with 2.2 mols of ethylene oxide.
TA-1: non-ionic surface-active agent of the formula:

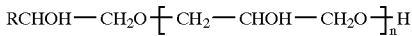

in which R=$C_9$–$C_2$ alkyl and n has an average statistical value of 3.5.
TA-2: non-ionic surface-active agent of the formula:

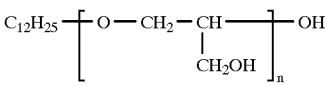

in which n has an average statistical value of 4.2.
ELA 12: polyoxyethyleneated lauryl alcohol containing 12 mols of ethylene oxide.
LIPOPROTEOL LCO: mixed sodium and triethanolamine salts of lipoaminoacids obtained by combining lauric acid with the aminoacids produced by the total hydrolysis of collagen, sold by Rhone-Poulenc
MIRANOL C.2M: cycloimidazoline derivative of coconut oil, sold by Miranol:

SANDOPAN DTC.AC: trideceth-7 carboxylic acid of the formula: $CH_3(CH_2)_{11}$—$CH_2$—$(OCH_2$—$CH_2)_6OCH_2$—COOH sold by SANDOZ.
POLAWAX GP 200: mixture of fatty alcohols and oxyethyleneated products, sold by Croda.
CELLOSIZE QP 4400 H: hydroxyethylcellulose having a viscosity of 4,400 cps at 25° C. in 2% strength aqueous solution, measured using a Brookfield No. 4 module.
AMMONYX 27: monoalkyltrimethylammonium chloride sold by Franconyx. Alkyl=radical derived from tallow.
LEXEIN X.250: hydrolysate of proteins derived from collagen, sold by Wilson.
LEXEIN S.620: potassium salt of a product resulting from the condensation of collagen protein and coconut fatty acid, having a molecular weight of 700–800 and sold by Inolex.
CSA 15 EO: oxyethyleneated cetyl/stearyl alcohol containing 15 mols of ethylene oxide.
PAQ-4: polymer of the formula:

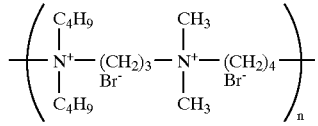

The disclosure of the patent specifications referred to herein are hereby all incorporated by reference.

We claim:
1. A composition for application to human hair which comprises, in a cosmetically suitable carrier or diluent:
a) at least one amphoteric polymer containing units A and B distributed in the polymer chain, where A denotes a unit derived from a monomer containing at least one basic nitrogen atom and B denotes a unit derived from an acid monomer containing one or more carboxyl or sulphonyl groups, or, alternatively, A and B denote a group derived from a zwitterionic carboxybetaine monomer; or A and B denote a cationic polymer chain containing secondary or tertiary amine groups or quaternary ammonium groups, in which chain at least one of the amine groups carries-a carboxyl or sulphonyl group joined via a hydrocarbon radical, or A and B form part of a polymer with alpha, beta-dicarboxyethylene units, in which one of the carboxyl groups has been reacted with a polyamine containing one or more primary or secondary amine groups, and
b) at least one cationic polyamine or poly-(quaternary ammonium) polymer selected from the group consist- ing of vinylpyrrolidone/aminoalcohol acrylate and methacrylate copolymers;
wherein the said amphoteric and cationic polymers are present in the amount of 0.01 to 10% by weight and having a molecular weight of 500 to 2,000,000, said composition containing essentially no anionic polymer.

2. A composition for application to human hair which comprises, in a cosmetically acceptable carrier or diluent:
   a) at least one amphoteric polymer containing units A and B distributed in the polymer chain, where A denotes a unit derived from a monomer containing at least one basic nitrogen atom and B denotes a unit derived from an acid monomer containing one or more carboxyl or sulphonyl groups, or, alternatively, A and B denote a group derived from a zwitterionic carboxybetaine monomer;
   b) at least one cationic polyamine or poly-(quaternary ammonium) polymer selected from the group consisting of:
      1) a quaternised or unquaternised vinylpyrrolidone polymer,
      2) a quaternised guar gum,
      3) a homo- or copolymer containing, as the main constituent of the chain, units corresponding to the formula VIII or VIII':

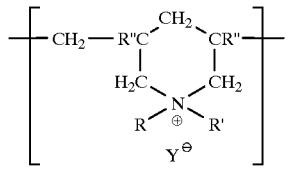

(VIII)

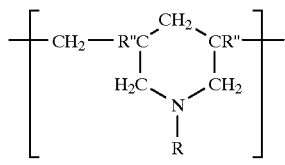

(VIII')

in which formulae R" denotes hydrogen or methyl, R and R' independently denote an alkyl group having from 1 to 22 carbon atoms, a hydroxyalkyl group, or a lower amidoalkyl group, or R and R', together with the nitrogen atom to which they are attached, denote a heterocyclic group,

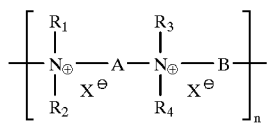

(IX)

in which $R_1$, $R_2$, $R_3$ and $R_4$, which are identical or different, represent an aliphatic, alicyclic or arylaliphatic radical containing a maximum of 20 carbon atoms, or a lower hydroxyaliphatic radical or alternatively $R_1$ and $R_2$, and $R_3$ and $R_4$, together or separately denote with the nitrogen atoms to which they are attached, a heterocyclic ring which optionally contains a second hetero-atom other than nitrogen, or alternatively, $R_1$, $R_2$, $R_3$ and $R_4$ represent a group of the formula:

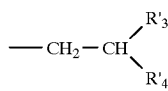

in which $R'_3$ denotes hydrogen or lower alkoxy and $R'_4$ denotes —CN, or a group

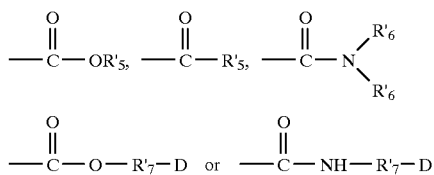

$R'_5$ denoting lower alkyl, $R'_6$ denoting hydrogen or lower alkyl, $R'_7$ denoting alkylene and D denoting a quaternary ammonium group, A and B independently represent polymethylene groups containing from 2 to 20 carbon atoms, which is linear or branched and saturated or unsaturated and optionally contain one or more chain aromatic rings or one or more groups —CH$_2$—Y—CH$_2$—, in which Y denotes O, S,

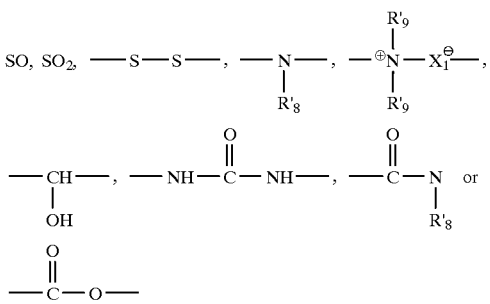

in which $X_1^\ominus$ denotes an anion derived from a mineral or organic acid, $R'_8$ denotes hydrogen or lower alkyl and $R'_9$ denotes lower alkyl, or alternatively A, $R_1$ and $R_3$, together with the two nitrogen atoms to which they are attached, form a piperazine ring; and
      5) a chitosan derivative
   wherein each of said amphoteric and cationic polymers is present in an amount of 0.5 to 5% by weight and having a molecular weight of 500 to 2,000,000,
   said composition containing essentially no anionic polymer.

3. A composition according to claim 2 in which the amphoteric polymer is selected from:
   1) a polymer resulting from the copolymerisation of a vinyl monomer carrying a carboxyl group and a basic substituted vinyl monomer containing at least one basic nitrogen atom,
   2) a polymer containing units derived from
      a) at least one acrylamide or methacrylamide substituted on the nitrogen by an alkyl radical,
      b) a least one acid comonomer containing one or more reactive carboxyl groups, and
      c) at least one basic acrylic or methacrylic comonomer, with a primary, secondary or tertiary amine substituent or quaternary ammonium substituent or the product resulting from the quaternisation of dimethylaminoethyl methacrylate with dimethyl or diethyl sulphate, 3) a polymer containing zwitterionic units, derived from the formula:

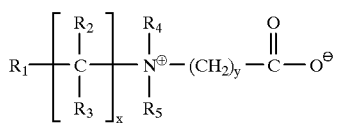

(III)

in which $R_1$ denotes a polymerisable unsaturated group, x and y independently represent an integer from 1 to 3, $R_2$ and $R_3$ independently represent hydrogen, methyl, ethyl or propyl, and $R_4$ and $R_5$ independently represent a hydrogen atom or an alkyl radical such that the sum of the carbon atoms in $R_4$ and $R_5$ does not exceed 10, 4) a polymer derived from chitosan and containing monomer units corresponding to the following formulae:

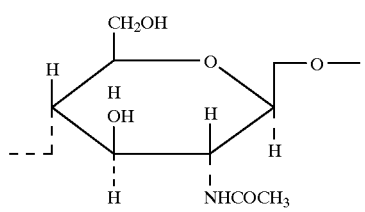

(A)

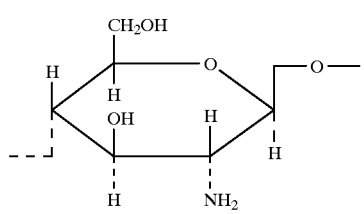

(B)

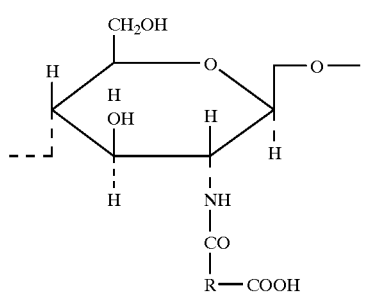

(C)

in which the relative proportions of the units are 0 to 30% of unit (A), 5 to 50% of unit (B) and 30 to 90% of unit (C) and R represents the radical of the formula:

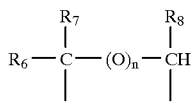

in which, if n is equal to 0, $R_6$, $R_7$ and $R_8$, which are identical or different, each represent a hydrogen atom, a methyl, hydroxyl, acetoxy or amino radical, a monoalkylamine radical or a dialkylamino radical, which optionally contains one or more chain nitrogen atoms and/or is optionally substituted by one or more amino, hydroxyl, carboxyl, alkylthio or sulphonyl groups, or an alkylthio radical in which the alkyl group carries an amino radical, at least one of the radicals $R_6$, $R_7$ and $R_8$ in this case being a hydrogen atom, or, if n is equal to 1, $R_6$, $R_7$ and $R_8$ each represent a hydrogen atom, or a basic or acid salt of a said polymer.

4. A composition according to claim 2 which has a pH of 2 to 11.

5. A composition according to claim 2 which contains at least one monoalcohol, polyalcohol or glycol ether, as solvent.

6. A composition according to claim 2 which contains at least one anionic, cationic, non-ionic or amphoteric surface-active agent or mixture thereof in the range of 3 to 50% by weight.

7. A composition according to claim 2 which is in the form of an aqueous, alcoholic or aqueous-alcoholic solution, a gel, a thickened lotion, an emulsion, a cream or a powder.

8. A composition according to claim 2 which contains at least one perfume, dyestuff for colouring the composition or the fibres treated, a preservative, sequestering agent, thickener, softener, foam stabiliser, sun filter or peptising agent.

9. A composition according to claim 2 for dyeing the hair which contains at least one oxidation dyestuff precursor and/or direct dyestuff.

10. A composition according to claim 2 for waving or straightening the hair which contains one or more reducing agents for the hair.

11. Process for the treatment of keratin fibres, which comprises applying thereto at least one composition as defined in claim 2.

12. Process according to claim 11 which comprises, after allowing the composition to impregnate the fibres, rinsing the fibres.

13. A composition according to claim 2 in which the amphoteric polymer is a polymer containing units derived from a) at least one acrylamide or methacrylamide substituted on the nitrogen by an alkyl radical, b) at least one acid comonomer containing one or more reactive carboxyl groups, and c) at least one basic acrylic or methacrylic comonomer, with a primary, secondary or tertiary amine substituent or a quaternary ammonium substituent or the product resulting from the quaternisation of dimethylaminoethyl methacrylate with dimethyl or diethyl sulphate.

14. A composition according to claim 2 in which the cationic polymer is a polymer of the formula:

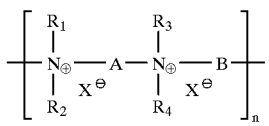

(IX)

wherein $R_1$, $R_2$, $R^3$ and $R_4$, which are identical or different, are selected from the group consisting of aliphatic, alicyclic or arylaliphatic containing a maximum of 20 carbon atoms, lower hydroxyaliphatic, and groups wherein $R_1$ and $R_2$, and $R_3$ and $R_4$, together or separately denote with the nitrogen atoms to which they are attached, a heterocyclic ring or a heterocyclic ring substituted by a second hetero-atom other than nitrogen, $R_1$, $R_2$, $R_3$ and $R_4$ represent a group of the formula:

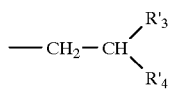

in which R'₃ denotes hydrogen or lower alkoxy and R'₄ denotes —CN, or a group

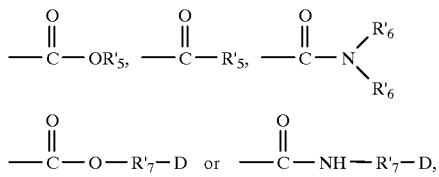

R'₅ denoting lower alkyl, R'₆ denoting hydrogen or lower alkyl, R'₇ denoting alkylene and D denoting a quaternary ammonium group, A and B independently represent polymethylene groups having from 2 to 20 carbon atoms, or polymethylene groups having from 2 to 20 carbon atoms substituted by one or more chain aromatic rings or one or more groups —CH₂—Y—CH₂—, in which Y denotes O, S, SO, SO₂, —S—S—,

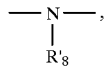

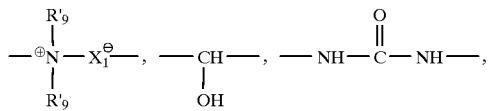

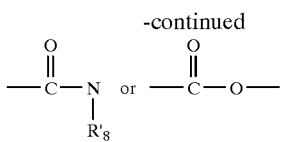

in which $X_1^{\ominus}$ denotes an anion derived from a mineral or organic acid, R'₈ denotes hydrogen or lower alkyl and R'₉ denotes lower alkyl, and wherein A, R₁ and R₃, together with the two nitrogen atoms to which they are attached, form a piperazine ring.

15. A composition according to claim 2 in which the quaternized or unquaternized vinylpyrrolidone polymer is a vinylpyrrolidone/aminoalcohol acrylate or methacrylate copolymer.

16. A composition according to claim 2 in which each of said amphoteric and cationic polymers is present in an amount from 0.5 to 5% by weight.

17. A composition for application to keratin fibres which comprises, in a cosmetically acceptable carrier or diluent:
  a) at least one amphoteric polymer containing units A and B distributed in the polymer chain, where A denotes a unit derived from a monomer containing at least one basic nitrogen atom and B denotes a unit derived from an acid monomer containing one or more carboxyl or sulphonyl groups, and
  b) at least one cationic poly(quaternary ammonium) polymer, containing ammonium groups in the polymer chain or joined to the latter, said cationic polymer being a cellulose ether derivative containing quaternary ammonium groups, wherein the said amphoteric and cationic polymers are present in an amount of 0.01 to 10% by weight, said composition containing essentially no anionic polymer.

* * * * *